(12) United States Patent
Fukuda et al.

(10) Patent No.: US 9,146,204 B2
(45) Date of Patent: Sep. 29, 2015

(54) X-RAY ANALYZING APPARATUS AND METHOD

(75) Inventors: Tomoyuki Fukuda, Takatsuki (JP); Kosuke Shimizu, Takatsuki (JP); Akihiro Ikeshita, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 14/350,866

(22) PCT Filed: Aug. 6, 2012

(86) PCT No.: PCT/JP2012/069979
§ 371 (c)(1),
(2), (4) Date: Apr. 10, 2014

(87) PCT Pub. No.: WO2013/073238
PCT Pub. Date: May 23, 2013

(65) Prior Publication Data
US 2015/0233845 A1   Aug. 20, 2015

(30) Foreign Application Priority Data

Nov. 14, 2011   (JP) ................ 2011-248202

(51) Int. Cl.
*G01N 23/20* (2006.01)
*G21K 1/06* (2006.01)
*G01N 23/223* (2006.01)
*G01N 23/22* (2006.01)

(52) U.S. Cl.
CPC ........ *G01N 23/223* (2013.01); *G01N 23/20008* (2013.01); *G01N 23/20016* (2013.01); *G01N 23/2204* (2013.01); *G21K 1/06* (2013.01); *G01N 23/20* (2013.01)

(58) Field of Classification Search
CPC ... G01N 23/00; G01N 23/20; G01N 23/2008; G01N 23/20016; G01N 23/205; G01N 23/2055; G01N 23/22; G01N 23/2204; G01N 23/223; G21K 1/06; A61B 6/483; A61B 6/485
USPC .................. 378/44–50, 70, 71, 78, 81–85
See application file for complete search history.

(56) References Cited

U.S. PATENT DOCUMENTS 5,148,457 A   9/1992   Kubota et al.

FOREIGN PATENT DOCUMENTS

| JP | 05-066204 A | 3/1993 |
|---|---|---|
| JP | 05-126768 A | 5/1993 |
| JP | 08-161049 A | 6/1996 |
| JP | 10-282022 A | 10/1998 |
| JP | 2002-005858 A | 1/2002 |
| JP | 2009-210507 A | 9/2009 |

OTHER PUBLICATIONS

Communication dated May 30, 2014, issued by the International Searching Authority, in counterpart Application No. PCT/JP2012/069979.

*Primary Examiner* — Anastasia Midkiff
(74) *Attorney, Agent, or Firm* — Sughrue Mion, PLLC

(57) ABSTRACT

An X-ray analyzing apparatus is such that a diffraction pattern, in which the intensity of secondary X-rays (4) is associated with the angle of rotation of a sample (S), is stored; while the pattern is scanned by a line of the secondary X-rays (4) intensity in a direction of highness and lowness, points on the pattern having not higher intensity than the line are taken as candidate points; respective angles of rotation of the candidate points, when the maximum value of the difference in angle of rotation between the neighboring candidate points attains a predetermined angle, are stored; depending on coordinates of a point of measurement, the angle of rotation proximate to the coordinates is read out from the stored angles; and the sample (S) is set to the read out angle and the point of measurement is arranged within the field of view (V) of a detector (7).

4 Claims, 6 Drawing Sheets

X-RAY ANALYZING APPARATUS AND METHOD

CROSS REFERENCE TO THE RELATED APPLICATION

This application is based on and claims Convention priority to Japanese patent application No. 2011-248202, filed Nov. 14, 2011, the entire disclosure of which is herein incorporated by reference as a part of this application.

BACKGROUND OF THE INVENTION

1. Field of the Invention

The present invention relates to an X-ray analyzing apparatus and a method therefor for measuring an arbitrary point of measurement of a disc shaped sample such as, for example, a wafer.

2. Description of Related Art

Hitherto, the analysis of, for example, a wafer has been carried out by irradiating a sample surface with primary X-rays, detecting secondary X-rays emanating from the sample surface and then measuring the intensity of the secondary X-rays emitted by the sample surface. In the practice of this conventional X-ray analysis, it has been well recognized that a sample of a kind having a crystalline structure, such as, for example, a wafer, when irradiated with the primary X-rays, may emit the secondary X-rays containing not only fluorescent X-rays, but also diffracted X-rays. During the X-ray fluorescence analysis, these diffracted X-rays often constitute an obstruction to the measurement and the rotative direction of the sample in which the diffracted X-rays are generated changes depending on the cut plane of the sample which may be (110) or (111) plane in the crystalline structure.

Accordingly, the fluorescence analyzing method has been known in which, prior to the X-ray fluorescence analysis of the sample, while the sample is rotated an angle equal to or greater than 180° about a predetermined point of the sample, the primary X-rays are radiated towards the sample, secondary X-rays emanating from the sample and containing fluorescent X-rays and diffracted X-rays are detected, the sample is then rotated in such a direction that the intensity of the detected secondary X-rays may exhibit the minimum value, and in this condition the sample is thereafter transferred in XY directions, which are perpendicular to each other, in a plane parallel to the measuring surface to perform the analysis over the entire measuring surface of the sample. In this respect, see, for example, the patent document 1 listed below.

Also, as shown in FIG. 11 of the accompanying drawings, when with respect to a desired point of measurement (measuring site) positioned in the vicinity of an edge of a plate-like sample measurement is carried out by positioning the point of measurement so that the primary X-rays 2 are radiated from outside of a region above the sample S and the primary X-rays 2 so radiated may undergo a total reflection towards such region, a portion of the primary X-rays 2 are radiated towards a vertical end face of the sample S, accompanied by emission of strong scattered X-rays 9 in all directions. A portion of the scattered X-rays so emitted forms a large background to the fluorescent X-rays to be measured.

In view of the foregoing, a total reflection X-ray fluorescence spectrometer has been made available, in which with respect to an arbitrary point of measurement located in the vicinity of the edge of the sample, measurement is carried out by positioning the point of measurement so that the primary X-rays 2 are radiated from the region above the sample S and the primary X-rays 2 so radiated may undergo a total reflection towards outside of such region, to thereby suppress the scattered X-rays emitted from the end face of the sample. In this respect, see, for example, the patent document 2 listed below.

Prior Art Literature

[Patent Document 1] JP Laid-open Patent Publication No. H05-126768
[Patent Document 2] JP Laid-open Patent Publication No. 2002-005858

Although the fluorescence analyzing method disclosed in the patent document 1 referred to above appears to be effective in avoiding the incidence of the diffracted X-rays generated from the sample of a kind having a crystalline structure of a rotational symmetry, such fluorescence analyzing method is incapable of avoiding the diffracted X-rays generated from the sample of a kind having its crystalline structure that is not of a rotational symmetry.

On the other hand, the total reflection X-ray fluorescence spectrometer disclosed in the patent document 2 referred to above appear to be effective in suppressing influences brought about by the scattered X-rays generated from the neighborhood of the sample, such total reflection X-ray fluorescence spectrometer has been found problematic in that since no attention is drawn to avoid the diffracted X-rays generated from the sample, no diffracted X-ray cannot be avoided even though the sample is set to a position effective to eliminate the influences brought about by the scattered X-rays, and, therefore, an accurate analysis cannot be accomplished depending on the sample.

SUMMARY OF THE INVENTION

In view of the foregoing, the present invention has been devised to eliminate the problems and inconveniences inherent in the prior art discussed above and is intended to provide an X-ray analyzing apparatus and method, which are effective to suppress and avoid the scattered X-rays and impurity X-rays (impurity lines) both generated from the neighborhood of an edge of a disc-shaped sample of a kind, having a crystalline structure, and apparatus structural components in the vicinity of the sample and also to circumvent the diffracted X-rays generated from the sample, to thereby facilitate an accurate analysis easily.

In order to accomplish the foregoing object, the present invention in accordance with a first aspect thereof provides an X-ray analyzing apparatus, which includes a sample table to support a disc-shaped sample of a kind, having a crystalline structure, placed thereon, an X-ray source to radiate primary X-rays, which have been monochromated, towards the sample, a detector to detect secondary X-rays generated from the sample, a parallel shifting unit to translate the sample table so that an arbitrary point of measurement on a measuring surface of the sample may be brought into a field of view of the detector, a rotating unit to rotate the sample table about an axis perpendicular to the measuring surface of the sample, and a control unit to control the X-ray source, the parallel shifting unit and the rotating unit, and in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region.

The control unit stores a predetermined angle which is of a value equal to or smaller than the angle 2θ1, determined by the following equation (1) on the basis of the radius R of the sample and the radius T of the field of view of the detector in the measuring surface of the sample, but not smaller than 4°.

$$\sin \theta 1 = (R-T)/R \tag{1}$$

The control unit referred to above operates in the following manner. At the outset, the monochromated primary X-rays are radiated from the X-ray source while the sample is rotated 360° about a predetermined point of the sample by the rotating unit, and a diffraction pattern, in which the intensity of the secondary X-rays of a wavelength of the monochromated primary X-rays detected by the detector is associated with the angle of rotation of the sample, is acquired and stored. Thereafter, while the diffraction pattern is scanned by a linear line representative of the intensity of the secondary X-rays in a direction of highness and lowness of the intensity, points on the diffraction pattern having the intensity not higher than the intensity represented by the linear line are taken as candidate points, and respective angles of rotation of the candidate points, when the maximum value of the difference in angle of rotation among the neighboring candidate points becomes to be the predetermined angle, are stored. Thereafter, depending on coordinates of the point of measurement of the sample, the angle of rotation most proximate to coordinates of the point of measurement is read out from the stored respective angles of rotation of the candidate points, the rotating unit and the parallel shifting unit are controlled so that the sample is set at the angle of rotation so read out and the point of measurement of the sample is arranged within the field of view of the detector.

Well, in order to suppress and avoid the scattered X-rays and the impurity X-rays generated from the neighborhood of the edge of the disc-shaped sample and the apparatus structural components in the vicinity of the sample, it is ideal to perform the measurement under a condition in which when viewed in a plane the direction of travel of the primary X-rays and the direction from the center of the sample to the point of measurement coincide with each other, that is, under a condition in which the angle of rotation of the sample from the initial condition coincides with the θ coordinate of the point of measurement in the R–θ coordinates of the sample. However, if the angle of rotation from that condition is within a range of ±θ1 determined by the previously discussed equation (1), the scattered X-rays and the impurity X-rays can be sufficiently suppressed and avoided.

On the other hand, if the angle of rotation of the sample under the ideal condition for suppressing and avoiding the scattered X-rays and the impurity X-rays both referred to above coincide with, for example, the angle of rotation at any peak of the diffraction pattern, it is necessary to rotate the sample from the ideal condition for suppressing and avoiding the scattered X-rays and other, in order to circumvent the diffracted X-rays generated from the sample. Since the width of a skirt of one peak profile in the diffraction pattern, when speaking in terms of the angle of rotation, is not smaller than 4°, it is an unlikely circumstance that the angle of further rotation for the purpose of avoiding the diffracted X-rays will become smaller than the range of ±2°.

In view of the above, in the X-ray analyzing apparatus designed in accordance with the first aspect of the present invention, the control unit stores a predetermined angle which is equal to or smaller than an angle 2θ1, but not smaller than 4° and by automatically acquiring a diffraction pattern and scanning it by a linear line representative of the intensity of the secondary X-rays in a direction of highness and lowness of the intensity, the candidate points, at which the diffracted X-rays can be avoided and adjoining each other at the predetermined angle or smaller at the angle of rotation on the diffraction pattern, followed by storage of the respective angles of rotation at that candidate points. And, depending on the coordinates of the point of measurement of the sample, one of the stored angles of rotation, which is most proximate to (or matching with) the coordinates of the point of measurement is read out, and the sample is set to the read out angle of rotation with the point of measurement of the sample arranged within the field of view of the detector.

As hereinabove described, according to the X-ray analyzing apparatus of the structure according to the first aspect of the present invention, since with respect to the arbitrary point of measurement lying in the vicinity of the edge of the sample, the sample can be set to the angle of rotation effective to avoid the diffracted X-rays within a range of the predetermined angle which center is the ideal condition for suppressing and avoiding the scattered X-rays and the impurity X-rays, not only can the scattered X-rays and the impurity X-rays generated from the neighborhood of the edge of the disc-shaped sample of a kind having the crystalline structure and the apparatus structural components in the vicinity of the sample be suppressed and avoided, but also the diffracted X-rays generated from the sample can be avoided, thus making it possible to achieve an accurate analysis easily.

The X-ray analyzing apparatus designed in accordance with the second aspect of the present invention differs from the X-ray analyzing apparatus, designed in accordance with the previously described first aspect of the present invention in respect of the operation of the control unit as discussed below. Specifically, the control unit employed in the X-ray analyzing apparatus according to the second aspect of the present invention is such that while the sample is rotated 360° about a predetermined point of the sample by the rotating unit, the sample is irradiated with the monochromated primary X-rays from the X-ray source and a diffraction pattern, in which the intensity ratio, which is the intensity of the secondary X-rays of a wavelength of the monochromated primary X-rays, detected by the detector, divided by the intensity of fluorescent X-rays from a principal component of the sample detected by the detector, is associated with the angle of rotation of the sample, is acquired and stored. Then, while the diffraction pattern is scanned by a linear line representative of the intensity of the secondary X-rays in a direction of highness and lowness of the intensity ratio, points on the diffraction pattern having the intensity ratio not higher than the intensity ratio represented by the linear line are taken as candidate points, and respective angles of rotation of the candidate points, when the maximum value of the difference in angle of rotation among the neighboring candidate points becomes to be the predetermined angle, are stored.

Thereafter, the operation, in which depending on coordinates of the point of measurement of the sample the angle of rotation most proximate to coordinates of the point of measurement is read out from the stored respective angles of rotation of the candidate points, the rotating unit and the parallel shifting unit are controlled so that the sample is set at the angle of rotation so read out and the point of measurement of the sample is arranged within the field of view of the detector, is similar to that performed by the control unit employed in the previously described X-ray analyzing apparatus according to the first aspect of the present invention. In other words, the X-ray analyzing apparatus designed according to the second aspect of the present invention makes use of the intensity ratio, which is the intensity of the secondary X-rays of the wavelength of the monochromated primary X-rays divided by the intensity of the fluorescent X-rays from the principal component of the sample, in place of the intensity of the second X-rays of the wavelength of the monochromated primary X-rays that is used in the previously described X-ray analyzing apparatus designed according to the first aspect of the present invention.

According to the X-ray analyzing apparatus according to the second aspect of the present invention, since with the fluorescent X-rays from the principal component of the sample taken as an internal standard line the intensity of the secondary X-rays of the wavelength of the monochromated primary X-rays is corrected, it is possible to eliminate any change in angle of incident of the primary X-rays upon the sample as a result of fluctuation of a shaft of the rotating unit to enable a further accurate diffraction pattern to be acquired and, accordingly, a further accurate analysis can be accomplished.

An X-ray analyzing method designed in accordance with a third aspect of the present invention makes use of an X-ray analyzing apparatus, which includes a sample table to support a disc-shaped sample of a kind having a crystalline structure, which has been placed on such sample table, an X-ray source to radiate monochromated primary X-rays towards the sample, a detector to detect secondary X-rays emitted from the sample, a parallel shifting unit to move in parallel the sample table to enable an arbitrary point of measurement of a measuring surface of the sample to be arranged within a field of view of the detector, and a rotating unit to rotate the sample table about an axis perpendicular to the measuring surface of the sample, and in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region.

In this X-ray analyzing method, a predetermined angle of a value, which is equal to or smaller than an angle $2\theta 1$ determined by the previously discussed equation (1) on the basis of the radius R of the sample and the radius T of the field of view of the detector in the measuring surface of the sample, but not smaller than 4°, is stored beforehand.

And, the following procedures are executed. At the outset, the monochromated primary X-rays are radiated from the X-ray source while the sample is rotated 360° by the rotating unit about a predetermined point of the sample, and a diffraction pattern, in which the intensity of the secondary X-rays of a wavelength of the monochromated primary X-rays detected by the detector is associated with the angle of rotation of the sample, is acquired and stored. Then, while the diffraction pattern is scanned by a linear line representative of the intensity of the secondary X-rays in a direction of highness and lowness of the intensity, points on the diffraction pattern having the intensity not higher than the intensity represented by the linear line are taken as candidate points, and respective angles of rotation of the candidate points, when the maximum value of the difference in angle of rotation among the neighboring candidate points becomes to be the predetermined angle, are stored. Thereafter, depending on coordinates of the point of measurement of the sample, the angle of rotation most proximate to coordinates of the point of measurement is read out from the stored respective angles of rotation of the candidate points, the sample is set at the angle of rotation so read out and the point of measurement of the sample is arranged within the field of view of the detector by the rotating unit and the parallel shifting unit, and measurement is then carried out.

The above described X-ray analyzing method according to the third aspect of the present invention differs from the X-ray analyzing apparatus in accordance with the first aspect of the present invention in respect of the category of invention, but can bring about functions and effects similar to those afforded by the X-ray analyzing apparatus according to the first aspect of the present invention.

The X-ray analyzing method according to a fourth aspect of the present invention differs from the previously described X-ray analyzing method according to the third aspect of the present invention in respect of the following procedures. Specifically, in the practice of the X-ray analyzing method according to the fourth aspect of the present invention, the monochromated primary X-rays are radiated from the X-ray source while the sample is rotated 360° by the rotating unit about a predetermined point of the sample, and a diffraction pattern, in which an intensity ratio, which is the intensity of the secondary X-rays of a wavelength of the monochromated primary X-rays detected by the detector, divided by the intensity of fluorescent X-rays from a principal component of the sample detected by the detector, is associated with the angle of rotation of the sample, is acquired and stored. Then, while the diffraction pattern is scanned by a linear line representative of the intensity ratio of the secondary X-rays in a direction of highness and lowness of the intensity ratio, points on the diffraction pattern having the intensity ratio not higher than the intensity ratio represented by the linear line are taken as candidate points, and respective angles of rotation of the candidate points, when the maximum value of the difference in angle of rotation among the neighboring candidate points becomes to be the predetermined angle, are stored.

The procedures, in which depending on coordinates of the point of measurement of the sample, the angle of rotation most proximate to coordinates of the point of measurement is read out from the stored respective angles of rotation of the candidate points, the sample is set at the angle of rotation so read out and the point of measurement of the sample is arranged within the field of view of the detector by the rotating unit and the parallel shifting unit, and measurement is then carried out, are similar to those performed in the practice of the previously described X-ray analyzing method according to the third aspect of the present invention. In other words, in the practice of the X-ray analyzing method according to the fourth aspect of the present invention, the intensity ratio, which is the intensity of the secondary X-rays of the wavelength of the monochromated primary X-rays divided by the intensity of the fluorescent X-rays from the principal component of the sample, is used in place of the intensity of the second X-rays of the wavelength of the monochromated primary X-rays that is used in the previously described X-ray analyzing method designed according to the third aspect of the present invention.

The above described X-ray analyzing method in accordance with the fourth aspect of the present invention differs from the X-ray an analyzing apparatus in accordance with the second aspect of the present invention in respect of the category of invention, but can bring about functions and effects similar to those afforded by the X-ray analyzing apparatus according to the second aspect of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF PREFERRED EMBODIMENTS

Figure 1:
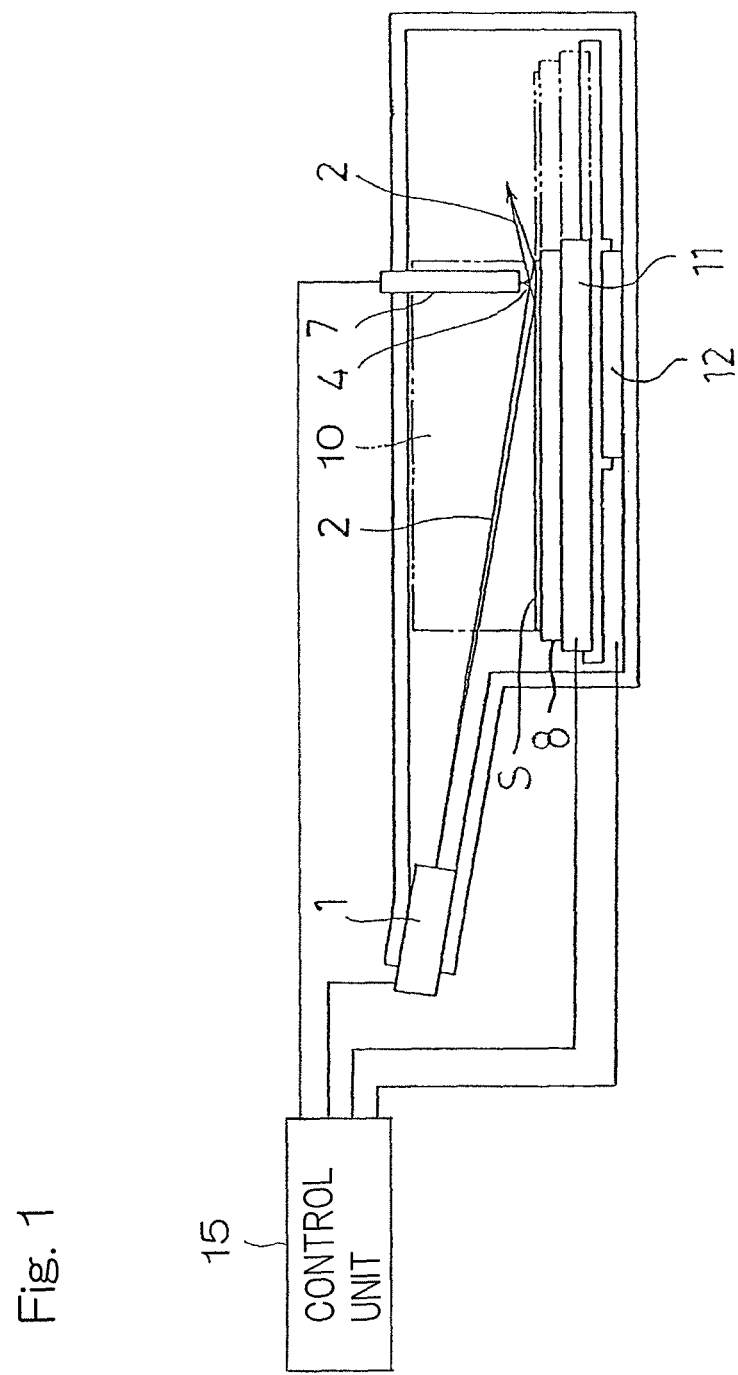
FIG. 1 is a schematic diagram showing an X-ray analyzing apparatus designed in accordance with a first preferred embodiment of the present invention.

Hereinafter, an X-ray analyzing apparatus designed in accordance with a preferred embodiment of the present invention will be described in detail. The X-ray analyzing apparatus is a total reflection X-ray fluorescence spectrometer which includes, as best shown in FIG. 1, a sample table 8 on which a disc-shaped sample S, such as, for example, a silicon wafer, of a kind having a crystalline structure is placed, an X-ray source 1 (including, for example, an X-ray tube and a spectroscopic device) to radiate primary X-rays 2, which have been monochromated, towards the sample S, a detector 7 to detect secondary X-rays 4, containing fluorescent X-rays, diffracted X-rays and others, which are generated from the sample S, and which is in the form of a semiconductor detector such as, for example, SDD, a parallel shifting unit 12 for translating the sample table 5 so that an arbitrary point of measurement on a measuring surface of the sample S may be disposed within the field of view V of the detector 7, more specifically at a position aligned with the center P of the field of view V of the detector 7, a rotating unit 11 to rotate the sample table 8 about an axis perpendicular to the measuring surface of the sample S, and a control unit 15 to control the X-ray source 1, the parallel shifting unit 12 and the rotating unit 11, and in which with respect to a certain arbitrary point of measurement lying in the neighborhood of an edge of the sample S, measurement is carried out by positioning the certain arbitrary point of measurement so that the monochromated primary X-rays 2 are radiated from a region 10 above the sample S and reflected towards outside of the region 10, in other words, the monochromated primary X-rays 2 are radiated from a left portion of the sheet of FIG. 1 towards the neighborhood of a right side edge of the sample S.

The X-ray source 1 and the detector 7 are fixed at respective predetermined position in the apparatus, and the monochromated primary X-rays 2, which have been generated from the X-ray source 1, are projected onto a center P of the field of view V of the detector 7 in the measuring surface of the sample S placed on the sample table 8. The parallel shifting unit 12 and the rotating unit 11 are operable to move and rotate the sample S, placed on the sample table 8, in a predetermined plane within the apparatus as shown by respective double dotted phantom lines in FIG. 1. Accordingly, even when the sample S is moved and rotated by the parallel shifting unit 12 and the rotating unit 11, the angle of incidence of the primary X-rays 2 from the X-ray source 1 relative to the measuring surface of the sample S and the intensity of radiation thereof remains constant and, at the same time, the dimensions and shape of the field of view V of the detector 7 in the measuring surface of the sample S also remain constant, the field of view V of the detector 7 represents a round shape of a radius T that is, for example, 10 mm.

In the instance now under discussion, the rotating unit 11 is operable to rotate the sample table 8 so that the sample S may be rotated about a center O of the sample S placed on the sample table 8. The parallel shifting unit 12 and the rotating unit 11 may be in the form of a positioning device of a type disclosed in, for example, the JP Laid-open Patent Publication No. H08-161049, that is, comprised of two arms (parallel shifting unit) and a sample table (rotating unit) which are so linked with each other as to perform a control of rotation independently by means of triple shafts. It is, however, to be noted that the parallel shifting unit 12 and the rotating unit 11 may be in the form of a so-called XYθ stage, that is, comprised of an XY stage (parallel shifting unit) and a θ stage (rotating unit) mounted on such XY stage. The parallel shifting unit 12 may be of a type capable of moving the sample S by itself without altering the direction of the sample S or of a type capable of drivingly cooperating with the rotating unit 11 to move the sample S without altering the direction of the sample S.

Figure 2:
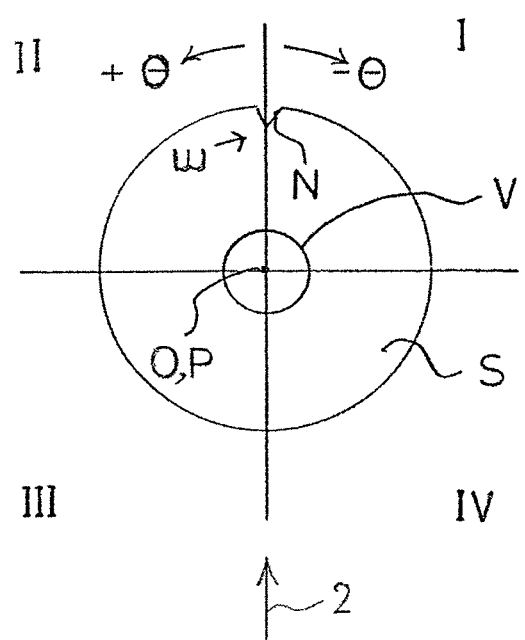
FIG. 2 is a diagram showing the initial position of a sample in the X-ray analyzing apparatus.

The sample S is placed on the sample table 8 and is, as shown in FIG. 2, set at an initial position with reference to a notch N or an orientation flat defined in the wafer forming the sample S. With the sample S held at the initial position, the center O of the sample S and the center P of the field of view V of the detector 7 are aligned with each other and the direction from the center O of the sample S towards the notch N and the direction of travel of the primary X-rays 2 when viewed in a plane are matched with each other. The position of the point of measurement in the sample S is expressed by, for example, an R–θ coordinates fixed on the measuring surface of the sample, in which the angle in a clockwise direction in the θ coordinate is expressed by a negative angle (−θ) whereas the angle in a counterclockwise direction in that θ coordinate is expressed by a positive angle (+θ), and the angle of rotation for the sample S being rotated by the rotating unit 11 is expressed by a symbol ω which takes a positive value when it is rotated in the clockwise direction.

In other words, a point of measurement C (shown in FIG. 6), which is defined at, for example, an edge of the sample S with the angle in the θ coordinate being −θ1, comes to occupy the position of the notch N at the initial position, shown in FIG. 2, when the sample S is rotated by the rotating unit 11 from the initial position by an angle of −θ1 in the θ coordinate. It is to be noted that in the θ coordinate the angle in the clockwise direction may be expressed by a positive value and, with respect to the angle of rotation of the sample S effected by the rotating unit 11, the counterclockwise direction may be expressed by a positive direction. Also, symbols I, II, III and IV employed in FIG. 2 represents the first quadrant, the second quadrant, the third quadrant and the fourth quadrant of the coordinate system, respectively.

The control unit 15 shown in FIG. 1 stores therein a predetermined angle α equal to or smaller than the angle 2θ1, determined by the following equation (1) on the basis of the radius R of the sample S and the radius T of the field of view V of the detector 7 in the measuring surface of the sample S, but not smaller than 4°.

$$\sin θ1 = (R−T)/R \qquad (1)$$

The significance of the angle 2θ1 will now be explained. For the sake of brevity, it is assumed that the sample S is moved without altering the direction of the sample S from the initial position, and two phantom lines (phantom linear lines) H and M, which are oriented in the same direction as a horizontal direction component of the primary X-rays 2 (when viewed in a plane, parallel to the direction of travel of the primary X-rays 2) and contact the field of view of the detector 7 in the measuring surface of the sample S, are taken into consideration. The direction of projection of the primary X-rays 2 and the field of view V of the detector 7 are fixed in the apparatus and, therefore, the two phantom lines H and M are also fixed in the apparatus. Relative to the fixed primary X-rays 2, the field of view V of the detector 7 and the two phantom lines H and M, the sample S is moved in this instance from the initial position without the direction of the sample S being altered and, for example, the point of measurement A lying at the edge of the sample S within the first quadrant is positioned at the center P of the field of view V of the detector 7 and, at the same time, the primary X-rays 2 are irradiated and measured.

Figure 5:
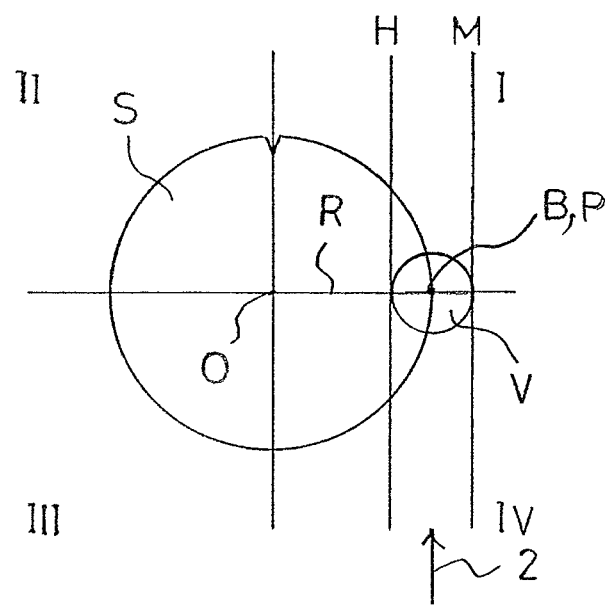
FIG. 5 is a diagram showing the relation in position between the sample and the phantom lines when another point of measurement B is similarly measured.

As shown in FIG. 5, when a point of measurement B (R, −90) lying at the edge of the sample S within the first quadrant is positioned at the center P of the field of view V of the detector 7 and measured, the right phantom line M lies outside the measuring surface of the sample S and the primary X-rays 2 impinge on a right edge of the sample S, resulting in generation of the scattered X-rays. Also, the primary X-rays 2 irradiates apparatus structural components present below the sample S (in an innermost direction of the sheet of FIG. 5) and scattered X-rays and impurity X-rays (fluorescent X-rays generated from the apparatus structural components present below the sample S) are generated. The initial scattered X-rays and impurity X-rays so generated in the manner described above further generate the scattered X-rays and impurity X-rays. Those scattered X-rays and those impurity X-rays are incident on the detector 7.

Figure 6:
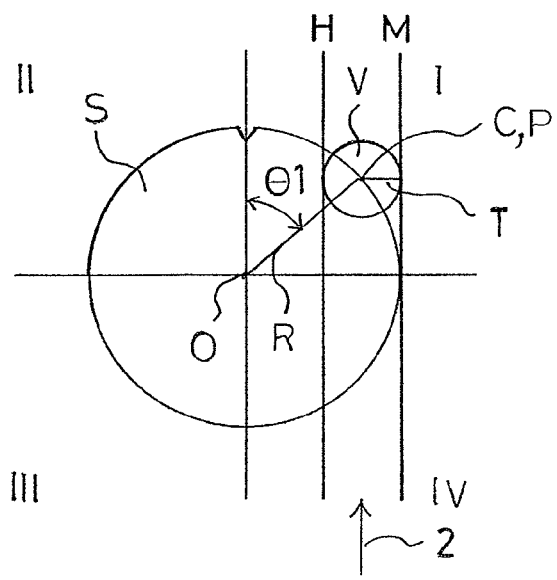
FIG. 6 is a diagram showing the relation in position between the sample and the phantom lines when a further point of measurement C is similarly measured.

On the other hand, as shown in FIG. 6, when the point of measurement C (R, −θ1) lying at the edge of the sample S within the first quadrant is positioned at the center P of the field of view V of the detector 7 and measured, the left phantom line H traverses the measuring surface of the sample S and the right phantom line M adjoins the measuring surface of the sample S. Accordingly, even though a portion of the primary X-rays 2 irradiate a right edge of the sample S and the apparatus structural components present below the sample S, the scattered X-rays and the impurity X-rays generated therefrom travel towards outside of the field of view V of the detector 7 and do not impinge upon the detector 7.

As hereinabove described, if the sample S is positioned so that both of the two phantom lines including the left phantom line H and the right phantom line M may lie on the measuring surface of the sample S (either traverse the measuring surface of the sample S or adjoin the measuring surface of the sample S), the scattered X-rays and the impurity X-rays can be prevented from being impinged upon the detector 7.

Figure 7:
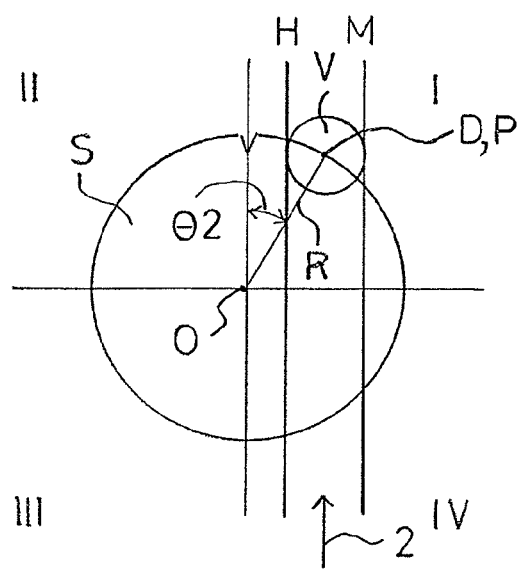
FIG. 7 is a diagram showing the relation in position between the sample and the phantom lines when a still further point of measurement D is similarly measured.

When a point of measurement D (R, −θ2) lying at the edge of the sample S within the first quadrant as shown in FIG. 7 is measured, both of the left and right phantom lines H and M lie on the measuring surface of the sample S while having traversed the measuring surface of the sample S and the angle θ1 of the point of measurement C, shown in FIG. 6, and the angle θ2 of the point of measurement D have such a relationship that the former is greater than the latter, that is, θ1>θ2.

As can readily be understood from the above, assuming that the sample S is moved from the initial position without the direction of such sample S being altered, with respect to the point of measurement lying in the vicinity of the edge of the sample S within the first quadrant, if the θ coordinate is within the range of θ to −θ1, the scattered X-rays and the impurity X-rays can be prevented from being incident upon the detector 7. Since this statement appears to be similarly applicable to the measurement of the point of measurement lying in the vicinity of the edge of the sample S within the second quadrant, it is possible to avoid the scattered X-rays and the impurity X-rays from being incident upon the detector 7 if the θ coordinate of the point of measurement is within the range of −θ1 to +θ1. The specific value of the angle θ1 can be determined from the equation (1) described hereinbefore. By way of example, assuming that the radius R of the sample S and the radius T of the field of view V of the detector 7 are 100 mm and 10 mm, respectively, the equation (1) will result in 64° as the specific value of the angle θ1 in this case.

Well, in the X-ray analyzing apparatus of the present invention, under ordinary circumstances the sample S can be moved while the direction of the sample S from the initial position is altered, and, at the time of measurement of the point of measurement in the vicinity of the edge of the sample S, for example, at the time of measurement of the point of measurement C (R, −θ1) shown in FIG. 6, it is ideal to perform the measurement under a condition, in which when viewed in a plane the direction of travel of the primary X-rays 2 and the direction from the center of the sample S towards the point of measurement C coincide with each other, that is, the angle of rotation of the sample S from the initial position shown in FIG. 2 coincide with the θ coordinate (−θ1) of the point of measurement C in the R−θ coordinates system of the sample S, in order to suppress and avoid the scattered X-rays and the impurity X-rays It is, however, to be noted that since as can readily be understood from the explanation made in connection with the movement of the sample S without the direction of the sample S from the above described initial position being altered, not only under the ideal condition described above, but if the angle of rotation from the initial position is within the range of +θ1, the measurement can be accomplished successfully even under such a condition as shown in FIG. 6 at the worst case it may occur in connection with suppression and avoidance of the scattered X-rays and the impurity X-rays, by moving the sample S without the direction of the sample S, after the latter has been rotated, being altered, and by positioning the point of measurement C at the center P of the field of view V of the detector 7, the scattered X-rays and the impurity X-rays can be sufficiently suppressed and avoided. This applies not only to the point of measurement C, but also to any arbitrarily chosen point of measurement lying in the vicinity of the edge for the sample S. In other words, with respect to the arbitrarily chosen point of measurement lying in the vicinity of the edge of the sample S, if the angle of rotation of the sample S lies within the range of 2θ1 which center is the angle of rotation of the sample S under the ideal condition for the suppression and avoidance of the scattered X-rays and the impurity X-rays, the scattered X-rays and the impurity X-rays can be sufficiently suppressed and avoided. The angle of 2θ1 referred to above, which is the upper limit value of the predetermined angle α that is beforehand stored in the control unit shown in FIG. 1 has such a significance as discussed above. The significance of the angle of 4°, which is the lower limit value of the predetermined angle α, will be discussed later.

Figure 3:
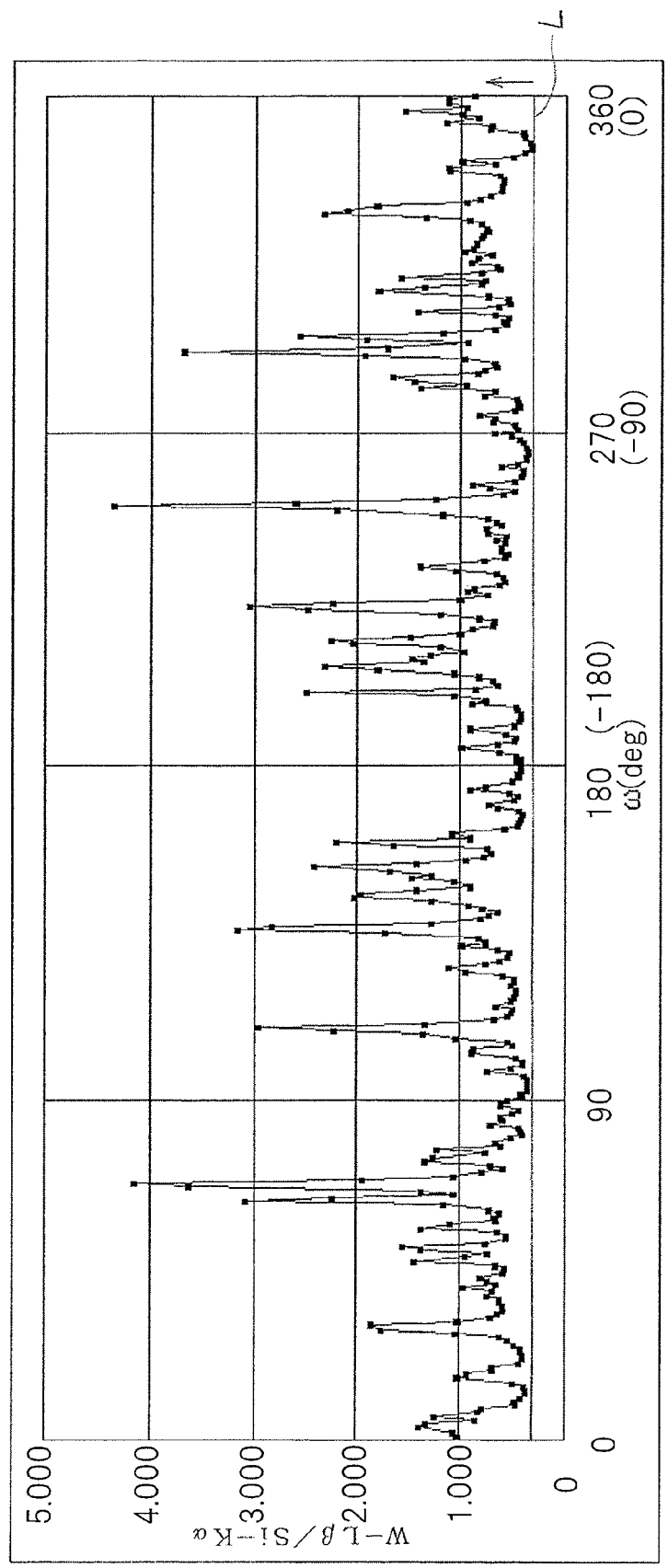
FIG. 3 is a chart showing an example of a diffraction pattern acquired by the X-ray analyzing apparatus.
Figure 4:
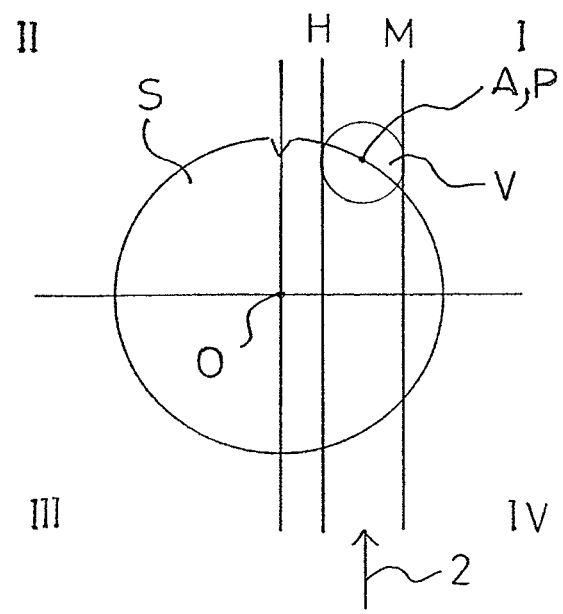
FIG. 4 is a diagram showing the relation in position between the sample and phantom lines when a point of measurement A is measured without changing the direction of the sample from the initial position by the X-ray analyzing apparatus.
Figure 8:
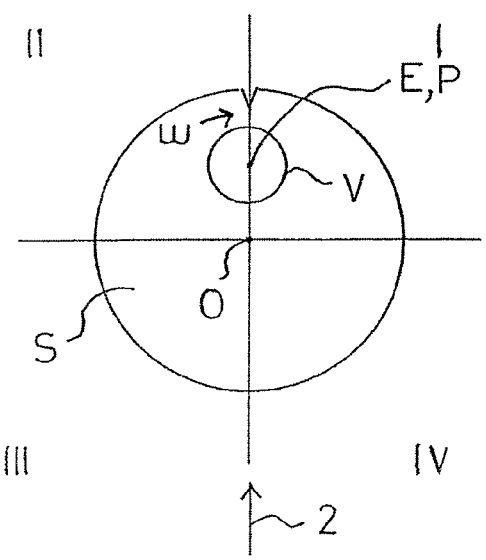
FIG. 8 is a diagram showing the sample set to a proper angle of rotation and position at the time acquisition of a diffraction pattern is started by the X-ray analyzing apparatus.

Referring again to FIG. 1, the control unit 15 storing the predetermined angle α operates in the following manner. At the outset, the sample S placed on the sample table 8 and then held at the initial position is moved without the direction of the sample S being altered and a point of measurement E (R1, 0) as shown in FIG. 8, where influence brought about by the scattered X-rays from the sample edge is small, is arranged at the center P of the field of view V of the detector (For example, R1=R/2). And, while the sample S is rotated 360° by the rotating unit 11 in the clockwise direction about the center O of the sample S, the monochromated primary X-rays 2 from the X-ray source 1 are radiated, and a diffraction pattern, in which an intensity ratio, which is the intensity of the secondary X-rays 4 of a wavelength of the monochromated primary X-rays detected by the detector 7, divided by the intensity of fluorescent X-rays 4 from a principal component of the sample S detected by the detector 7, is associated with the angle of rotation of the sample S, is acquired and stored. In the apparatus designed according to the embodiment now under discussion, W-Lβ line is radiated as the monochromated primary X-rays 2 and the intensity of the W-Lβ line is measured as the intensity of the secondary X-rays of the wavelength of the monochromated primary X-rays and, at the same time, the intensity of Si-Kα line is measured as the intensity of the fluorescent X-rays 4 from the principal component of the sample S and an example of the acquired diffraction pattern is shown in FIG. 3, in which the ordinate axis represents the intensity ratio of (the intensity of the W-Lβ line)/(the intensity of the Si-Kα line) and the abscissa axis represents the angle of rotation ω of the sample S.

The reason for the use of the intensity ratio, which is the intensity of the secondary X-rays 4 of the wavelength of the monochromated primary X-rays divided by the intensity of the fluorescent X-rays 4 from the principal component of the sample S, in this instance is because by correcting the intensity of the secondary X-rays 4 of the wavelength of the monochromated primary X-rays with the fluorescent X-rays 4 from the principal component of the sample S taken as an internal standard line, influences brought about by a change in angle of incidence of the primary X-rays 2 upon the sample S, which results from fluctuation of a shaft of the rotating unit 11, are eliminated to allow a further accurate diffraction pattern to be acquired, but where such correction is not so important, the intensity of the secondary X-rays 4 of the wavelength of the primary X-rays themselves, for example, the intensity of the W-Lβ line themselves can be employed in place of the intensity ratio that is divided by the intensity of the internal standard line. In this case, the monochromated primary X-rays 2 from the X-ray source 1 are radiated while the sample S is rotated 360° by the rotating unit 11 about the center O of such sample S in the clockwise direction and the diffraction pattern, in which the intensity of the secondary X-rays 4 of the wavelength of the monochromated primary X-rays detected by the detector 7 is associated with the angle of rotation ω of the sample S, is acquired and stored, in which pattern the ordinate axis represents, for example, the intensity of the W-Lβ line. It is to be noted that it may occur that for the monochromated primary X-rays 2, a predetermined wavelength portion of continuous X-rays emitted from the X-ray tube will be used other than characteristic X-rays, such as the W-Lβ line emitted from the X-ray tube.

Well, if the angle of rotation of the sample S under the ideal condition for suppressing and avoiding the scattered X-rays and the impurity X-rays as hereinbefore discussed matches with the angle of rotation at, for example, either any peak or near it in the acquired diffraction pattern, it is necessary to rotate the sample S from the ideal condition in order to suppress and avoid the scattered X-rays and others, so that the diffracted X-rays emitted from the sample S can be avoided. In general, the width of a skirt of one peak profile in the diffraction pattern, when speaking in terms of the angle of rotation, is not smaller than 4° and, therefore, it is an unlikely circumstance that the angle of further rotation for the purpose of avoiding the diffracted X-rays will become smaller than the range of ±2°. In other words, with respect to a certain arbitrary point of measurement lying in the vicinity of the edge of the sample S, unless the angle of rotation of the sample S is within the range equal to or greater than 4° which center is the angle of rotation of the sample S under the ideal condition for suppressing and avoiding the scattered X-rays and the impurity X-rays, it is not possible to avoid the diffracted X-rays emitted from the sample S. The angle of 4°, which is the lower limit value of the predetermined angle α stored in the control unit 15 shown in FIG. 1, has such a significance as discussed above.

It is to be noted that although the predetermined angle α stored in the control unit 15 is preferably large for the purpose of avoiding the diffracted X-rays, it is to be properly selected to be of a value equal to 2θ1 or smaller, but not smaller than 4° in consideration of, for example, mechanical structures of the X-ray analyzing apparatus. The diameters of silicon wafers, liquid crystal glasses, hard discs, magnetic discs and so on, which are the sample S of a kind having the crystalline structure, are standardized in the semiconductor industries to be 50 mm (2 inches), 76 mm (3 inches), 100 mm, 125 mm, 150 mm, 200 mm, 300 mm and so on, and since the radius T of the field of view V of the detector 7 is, for example, about 10 mm, it is actually possible to properly select the predetermined angle α from the range of the angle equal to or smaller than 2θ1, but not smaller than 4°.

Also, where the analysis of a plurality of samples S differing in size from each other is expected, the predetermined angles α1, α2, α3, . . . and αn for each of the sizes of the samples S may be selected and stored in the control unit 15 or, alternatively, while the predetermined angle α for the minimum size of the sample, of which range of selection is smallest, for example, 40° is applied to all of the sizes of the samples S, only such predetermined angle α may be stored in the control unit 15.

In the next place, by the control unit 15, while the diffraction pattern shown in FIG. 3 is scanned in a direction of highness and lowness of the intensity ratio, for example, from the side of the low intensity ratio by a linear line L parallel to the abscissa axis, which shows the intensity ratio referred to above, that is, the intensity of the W-Lβ line divided by the intensity of the Si-Kα line, all of points on the diffraction pattern which have an intensity ratio not higher than the intensity ratio represented by the linear line L are taken as candidate points, when the maximum value of the difference in angle of rotation between the neighboring candidate points attains the predetermined angle α, for example, the maximum value decreases down to the predetermined angle α, the control unit 15 stores respective angles of rotation at the candidate points at that time. The scanning from the low intensity ratio side may be started from the zero intensity ratio or from the minimum intensity ratio in the diffraction pattern. Although the diffraction pattern contains a portion where the candidate points are either continuous or interrupted, even at that interrupted portion the difference in angle of rotation between the neighboring candidate points attains a value smaller than the predetermined angle α. The candidate points are in actuality determined with a mechanical positioning error or the like taken into consideration.

It is to be noted that as hereinbefore described, where in place of the intensity ration which is divided by the intensity of the internal standard line the intensity of the secondary X-rays 4 of the wavelength of the monochromated primary X-rays themselves, for example, the intensity of the W-Lβ line themselves is used, the control unit 15 takes all of the points on the diffraction pattern having an intensity not higher than the intensity represented by the linear line L as candidate points while scanning the diffraction pattern in the direction of highness and lowness of the intensity, for example, from the low intensity side by the linear line L parallel to the abscissa axis which represents the intensity of the secondary X-rays 4, that is, the W-Lβ line.

The point of measurement of the sample S is inputted by means of an input unit such as, for example, a keyboard, a mouse and/or a touch panel, all now shown, and depending on coordinates of the point of measurement of the sample S the control unit 15 read out one of the angles of rotation of the stored candidate points, which is most proximate to the coordinates of the point of measurement, then controls the rotating unit 11 and the parallel shifting unit 12, sets the sample S at the angle of rotation so read out, and the point of measurement of the sample S is arranged at the center P of the field of view V of the detector 7 so that it can be measured.

Figure 9:
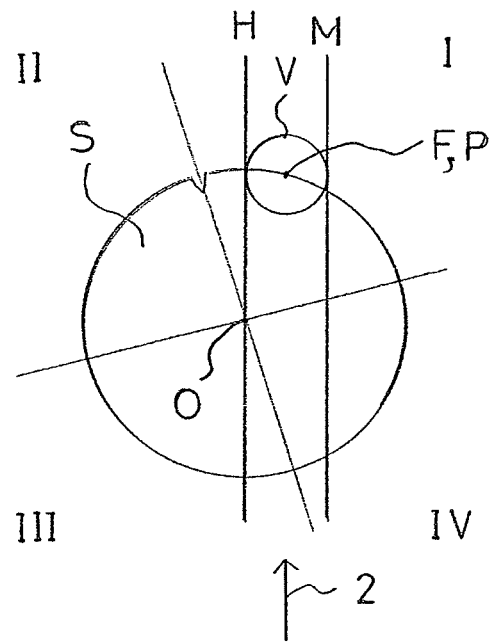
FIG. 9 is a diagram showing the sample set to a proper angle of rotation and position at the time of measurement of a point of measurement F by the X-ray analyzing apparatus.
Figure 10:
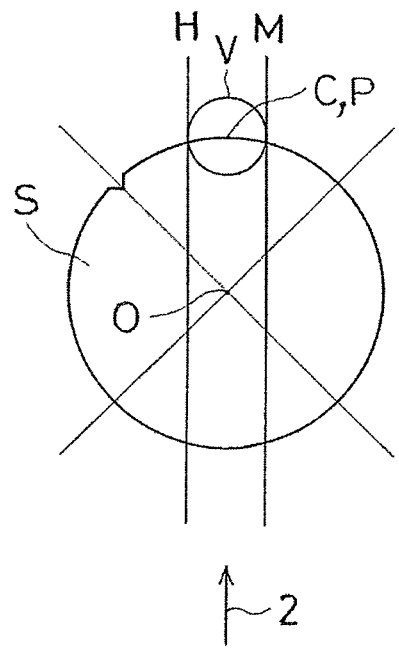
FIG. 10 is a diagram showing a condition of the sample that is considered ideal for suppressing and avoiding scattered X-rays and impurity X-rays at the time of measurement of the point of measurement C.
Figure 11:
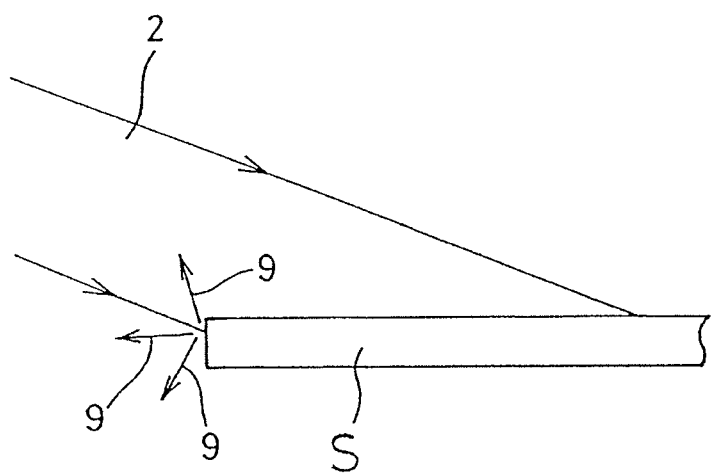
FIG. 11 is an enlarged view showing a scattered X-rays generating portion of a sample in the conventional X-ray analyzing apparatus.

By way of example, when a point of measurement F (R, −30) shown in FIG. 9 is to be measured, the angle of rotation (including −30 itself within the range of −30±α), which is most proximate to the θ coordinate (−30) of the point of measurement is read out from the stored angles of rotation of the candidate points and, if it is, for example, −15° (345°), the rotating unit 11 and the parallel shifting unit 12 are controlled to set the sample S at the read out angle of rotation −15° and the point of measurement F is arranged at the center P of the field of view V of the detector 7 to condition the sample S as shown in FIG. 9. And, the primary X-rays 2 are radiated from the X-ray source 1 towards the point of measurement F and the secondary X-rays 4 emanating from the sample S are then measured by the detector 7. The condition of the sample S before the latter is conditioned as shown in FIG. 9 may be the initial position as shown in FIG. 2 or may remain in a condition left upon completion of the measurement of a different point of measurement. Also, from such a condition the rotating unit 11 and the parallel shifting unit 12 may be operated in any manner and procedure provided that the sample S can be finally set to the condition shown in FIG. 9. Even points of measurement other than the neighborhood of the edge of the sample S are similarly measured. Results of measurement are displayed by means of a display unit such as, for example, a liquid crystal display device.

As hereinabove fully described, according to the X-ray analyzing apparatus designed in accordance with the preferred embodiment of the present invention, since with respect to the arbitrary point of measurement lying in the vicinity of the edge of the sample S, the sample S can be set to the angle of rotation effective to avoid the diffracted X-rays within a range of the predetermined angle α which center is the ideal condition for suppressing and avoiding the scattered X-rays and the impurity X-rays, not only can the scattered X-rays and the impurity X-rays generated from the neighborhood of the edge of the disc-shaped sample S of a kind having the crystalline structure and the apparatus structural components in the vicinity of the sample S be suppressed and avoided, but also the diffracted X-rays generated from the sample S can be avoided, thus making it possible to achieve an accurate analysis easily.

Also, an X-ray analyzing method, in which with the use of, for example, the X-ray analyzing apparatus of the construction designed in accordance with the preferred embodiment of the present invention, the predetermined angle α referred to above is stored and, following procedures which have been explained in connection with the operation of the control unit 15, the angle of rotation of the sample S is set with respect to the arbitrary point of measurement of the sample S, the point of measurement of the sample S is arranged at the center P of the field of view V of the detector 7 and the measurement is thereafter carried out, should be understood as encompassed within the scope of the present invention as an additional preferred embodiment thereof.

Although in describing the X-ray analyzing apparatus according to the preferred embodiment of the present invention, reference has been made to the total reflection X-ray fluorescence spectrometer, the X-ray analyzing apparatus of the present invention can be an energy dispersive fluorescence spectrometer, which is not a total reflection type, or a wavelength dispersive fluorescent spectrometer. Also, it may be a composite X-ray analyzing apparatus, in which a fluorescence spectrometer, an X-ray reflectance measuring apparatus and an X-ray diffractometer are combined.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . X-ray source
2 . . . Primary X-rays
4 . . . Secondary X-rays
7 . . . Detector
8 . . . Sample table
10 . . . Region above the sample
11 . . . Rotating unit
12 . . . Parallel shifting unit
15 . . . Control unit
A~F . . . Point of measurement of the sample
L . . . Linear line descriptive of the intensity or the intensity ratio of the secondary X-rays
R . . . Radius of the sample
S . . . Sample
T . . . Radius of field of view of the detector
V . . . Field of view of the detector
ω . . . Angle of rotation of the sample

What is claimed is:

1. An X-ray analyzing apparatus which comprises:

a sample table to support a disc-shaped sample of a kind having a crystalline structure, which has been placed on such sample table;

an X-ray source to radiate monochromated primary X-rays towards the sample;

a detector to detect secondary X-rays emitted from the sample;

a parallel shifting unit to move in parallel the sample table to enable an arbitrary point of measurement of a measuring surface of the sample to be arranged within a field of view of the detector;

a rotating unit to rotate the sample table about an axis perpendicular to the measuring surface of the sample; and a control unit to control the X-ray source, the parallel shifting unit and the rotating unit;

in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region;

in which the control unit stores a predetermined angle of a value which is equal to or smaller than an angle 2θ1 determined by the following equation (1) on the basis of the radius R of the sample and the radius T of the field of view of the detector in the measuring surface of the sample, but not smaller than 4°;

$$\sin \theta 1=(R-T)/R \qquad (1)$$

in which by the control unit, the monochromated primary X-rays are radiated from the X-ray source while the sample is rotated 360° by the rotating unit about a predetermined point of the sample, and a diffraction pattern, in which the intensity of the secondary X-rays of a wavelength of the monochromated primary X-rays detected by the detector is associated with the angle of rotation of the sample, is acquired and stored;

in which by the control unit, while the diffraction pattern is scanned by a linear line representative of the intensity of the secondary X-rays in a direction of highness and lowness of the intensity, points on the diffraction pattern having the intensity not higher than the intensity represented by the linear line are taken as candidate points, and respective angles of rotation of the candidate points, when the maximum value of the difference in angle of rotation among the neighboring candidate points becomes to be the predetermined angle, are stored; and in which depending on coordinates of the point of measurement of the sample, the angle of rotation most proximate to coordinates of the point of measurement is read out from the stored respective angles of rotation of the candidate points, the rotating unit and the parallel shifting unit are controlled so that the sample is set at the angle of rotation so read out and the point of measurement of the sample is arranged within the field of view of the detector.

2. An X-ray analyzing apparatus which comprises:

a sample table to support a disc-shaped sample of a kind having a crystalline structure, which has been placed on such sample table;

an X-ray source to radiate monochromated primary X-rays towards the sample;

a detector to detect secondary X-rays emitted from the sample;

a parallel shifting unit to move in parallel the sample table to enable an arbitrary point of measurement of a measuring surface of the sample to be arranged within a field of view of the detector;

a rotating unit to rotate the sample table about an axis perpendicular to the measuring surface of the sample; and a control unit to control the X-ray source, the parallel shifting unit and the rotating unit;

in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region;

in which the control unit stores a predetermined angle of a value which is equal to or smaller than an angle 2θ1 determined by the following equation (1) on the basis of the radius R of the sample and the radius T of the field of view of the detector in the measuring surface of the sample, but not smaller than 4°;

$$\sin \theta 1=(R-T)/R \qquad (1)$$

in which by the control unit, the monochromated primary X-rays are radiated from the X-ray source while the sample is rotated 360° by the rotating unit about a predetermined point of the sample, and a diffraction pattern, in which an intensity ratio, which is the intensity of the secondary X-rays of a wavelength of the monochromated primary X-rays detected by the detector, divided by the intensity of fluorescent X-rays from a principal component of the sample detected by the detector, is associated with the angle of rotation of the sample, is acquired and stored;

in which by the control unit, while the diffraction pattern is scanned by a linear line representative of the intensity ratio of the secondary X-rays in a direction of highness and lowness of the intensity ratio, points on the diffraction pattern having the intensity ratio not higher than the intensity ratio represented by the linear line are taken as candidate points, and respective angles of rotation of the candidate points, when the maximum value of the difference in angle of rotation among the neighboring candidate points becomes to be the predetermined angle, are stored; and in which depending on coordinates of the point of measurement of the sample, the angle of rotation most proximate to coordinates of the point of measurement is read out from the stored respective angles of rotation of the candidate points, the rotating unit and the parallel shifting unit are controlled so that the sample is set at the angle of rotation so read out and the point of measurement of the sample is arranged within the field of view of the detector.

3. An X-ray analyzing method using an X-ray analyzing apparatus which comprises:

a sample table to support a disc-shaped sample of a kind having a crystalline structure, which has been placed on such sample table;

an X-ray source to radiate monochromated primary X-rays towards the sample;

a detector to detect secondary X-rays emitted from the sample;

a parallel shifting unit to move in parallel the sample table to enable an arbitrary point of measurement of a measuring surface of the sample to be arranged within a field of view of the detector; and a rotating unit to rotate the sample table about an axis perpendicular to the measuring surface of the sample;

in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region;

in which a predetermined angle of a value which is equal to or smaller than an angle $2\theta 1$ determined by the following equation (1) on the basis of the radius R of the sample and the radius T of the field of view of the detector in the measuring surface of the sample, but not smaller than 4°, is stored;

$$\sin \theta 1 = (R-T)/R \qquad (1)$$

in which the monochromated primary X-rays are radiated from the X-ray source while the sample is rotated 360° by the rotating unit about a predetermined point of the sample, and a diffraction pattern, in which the intensity of the secondary X-rays of a wavelength of the monochromated primary X-rays detected by the detector is associated with the angle of rotation of the sample, is acquired and stored;

in which while the diffraction pattern is scanned by a linear line representative of the intensity of the secondary X-rays in a direction of highness and lowness of the intensity, points on the diffraction pattern having the intensity not higher than the intensity represented by the linear line are taken as candidate points, and respective angles of rotation of the candidate points, when the maximum value of the difference in angle of rotation among the neighboring candidate points becomes to be the predetermined angle, are stored; and in which depending on coordinates of the point of measurement of the sample, the angle of rotation most proximate to coordinates of the point of measurement is read out from the stored respective angles of rotation of the candidate points, the sample is set at the angle of rotation so read out and the point of measurement of the sample is arranged within the field of view of the detector by the rotating unit and the parallel shifting unit.

4. An X-ray analyzing method using an X-ray analyzing apparatus which comprises:

a sample table to support a disc-shaped sample of a kind having a crystalline structure, which has been placed on such sample table;

an X-ray source to radiate monochromated primary X-rays towards the sample;

a detector to detect secondary X-rays emitted from the sample;

a parallel shifting unit to move in parallel the sample table to enable an arbitrary point of measurement of a measuring surface of the sample to be arranged within a field of view of the detector; and a rotating unit to rotate the sample table about an axis perpendicular to the measuring surface of the sample;

in which with respect to a certain arbitrary point of measurement lying in the neighborhood of an edge of the sample, measurement is carried out by positioning the certain arbitrary point of measurement so that the monochromated primary X-rays are radiated from a region above the sample and reflected towards outside of the region;

in which a predetermined angle of a value which is equal to or smaller than an angle $2\theta 1$ determined by the following equation (1) on the basis of the radius R of the sample and the radius T of the field of view of the detector in the measuring surface of the sample, but not smaller than 4°, is stored;

$$\sin \theta 1 = (R-T)/R \qquad (1)$$

in which the monochromated primary X-rays are radiated from the X-ray source while the sample is rotated 360° by the rotating unit about a predetermined point of the sample, and a diffraction pattern, in which an intensity ratio, which is the intensity of the secondary X-rays of a wavelength of the monochromated primary X-rays detected by the detector, divided by the intensity of fluorescent X-rays from a principal component of the sample detected by the detector, is associated with the angle of rotation of the sample, is acquired and stored;

in which while the diffraction pattern is scanned by a linear line representative of the intensity ratio of the secondary X-rays in a direction of highness and lowness of the intensity ratio, points on the diffraction pattern having the intensity ratio not higher than the intensity ratio represented by the linear line are taken as candidate points, and respective angles of rotation of the candidate points, when the maximum value of the difference in angle of rotation among the neighboring candidate points becomes to be the predetermined angle, are stored; and in which depending on coordinates of the point of measurement of the sample, the angle of rotation most proximate to coordinates of the point of measurement is read out from the stored respective angles of rotation of the candidate points, the sample is set at the angle of rotation so read out and the point of measurement of the sample is arranged within the field of view of the detector by the rotating unit and the parallel shifting unit.

* * * * *